(12) United States Patent
Donzier et al.

(10) Patent No.: US 9,863,244 B2
(45) Date of Patent: Jan. 9, 2018

(54) DOWNHOLE FLUID PROPERTIES ANALYSIS PROBE, TOOL AND METHOD

(71) Applicant: OPENFIELD, Versailles (FR)

(72) Inventors: Eric Donzier, Bercheres sur Vesgre (FR); Linda Abbassi, Montigny le Bretonneux (FR); Emmanuel Tavernier, Paris (FR)

(73) Assignee: OPENFIELD, Versilles (FR)

( * ) Notice: Subject to any disclaimer, the term of this patent is extended or adjusted under 35 U.S.C. 154(b) by 0 days.

(21) Appl. No.: 15/062,128

(22) Filed: Mar. 6, 2016

(65) Prior Publication Data

US 2017/0198574 A1 Jul. 13, 2017

(30) Foreign Application Priority Data

Jan. 8, 2016 (EP) ..................................... 16305013

(51) Int. Cl.
*E21B 49/08* (2006.01)
*G01N 21/64* (2006.01)
(Continued)

(52) U.S. Cl.
CPC ............. *E21B 49/08* (2013.01); *G01N 21/55* (2013.01); *G01N 21/64* (2013.01); *G01N 33/28* (2013.01)

(58) Field of Classification Search
CPC ...................................................... E21B 49/08
See application file for complete search history.

(56) References Cited

U.S. PATENT DOCUMENTS 4,547,774 A * 10/1985 Gould .................... E21B 17/023
250/263
5,912,459 A 5/1999 Mullins et al.
(Continued)

FOREIGN PATENT DOCUMENTS

EP 0392741 A2 10/1990
WO WO0120322 A1 3/2001

OTHER PUBLICATIONS

PCT/EP2017/050288, International Search Report, dated Apr. 4, 2017, European Patent Office, P.B. 5818 Patentlaan 2 NL—2280 HV Rijswijk.

(Continued)

*Primary Examiner* — David Porta
*Assistant Examiner* — Hugh H Maupin
(74) *Attorney, Agent, or Firm* — The Jansson Firm; Pehr B. Jansson

(57) ABSTRACT

A downhole fluid properties optical analysis probe (1) to analyze at least one property of a multiphase flow mixture (100) flowing in a hydrocarbon well (51) has an elongated cylindrical body shape and comprises an optical tip (5) at one end of the elongated cylindrical body arranged to be in contact with the multiphase flow mixture (100), and an optoelectronics module (11) at another end of the elongated cylindrical body arranged to be separated from the multiphase flow mixture (100) and coupled to the optical tip (5) by an optical fiber bundle. The optoelectronics module (11) comprises at least one light source (13) arranged to emit electromagnetic radiations in a wavelength range such that reflectance occurs when gas (G) is present at the optical tip (5) and fluorescence occurs when oil (O) is present at the optical tip (5), at least one reflectance light detector (14) arranged to be responsive to a reflectance light and to provide a reflectance signal (U1($t$)) and at least one fluorescence light detector (15) arranged to be responsive to a fluorescence light and to provide a fluorescence signal (U2($t$)). The optical fiber bundle comprises at least one first optical fiber (6) coupling the light source (13) to the optical tip (5), at least one second optical fiber (7) coupling the optical tip (5) to the reflectance light detector (14), and at least one third optical fiber (8) coupling the optical tip (5) to the fluorescence light detector (15), the at least one first, second and third optical fibers being mounted together into a protective tube (9) resistant to downhole conditions.

15 Claims, 4 Drawing Sheets

(51) Int. Cl.
*G01N 21/55* (2014.01)
*G01N 33/28* (2006.01)

(56) References Cited

U.S. PATENT DOCUMENTS

| | | | |
|---|---|---|---|
| 6,023,340 | A | 2/2000 | Wu et al. |
| 6,075,611 | A * | 6/2000 | Dussan V. ............. G01F 1/7086 356/432 |
| 2002/0118905 | A1 | 8/2002 | Wu et al. |
| 2003/0029995 | A1 * | 2/2003 | Mullins ................ G01F 1/7086 250/302 |
| 2007/0006663 | A1 * | 1/2007 | Zerwekh ............ G01K 11/3206 73/800 |
| 2007/0190819 | A1 | 8/2007 | Kariya et al. |
| 2013/0016336 | A1 * | 1/2013 | Xie ........................ G01N 21/33 356/51 |
| 2014/0264077 | A1 * | 9/2014 | Tokhtuev ............ G01N 21/645 250/458.1 |

OTHER PUBLICATIONS

PCT/EP2017/050288, Written Opinion of the International Searching Authority, dated Apr. 4, 2017, European Patent Office, Gitschiner Str. 103 D-10958 Berlin.

* cited by examiner

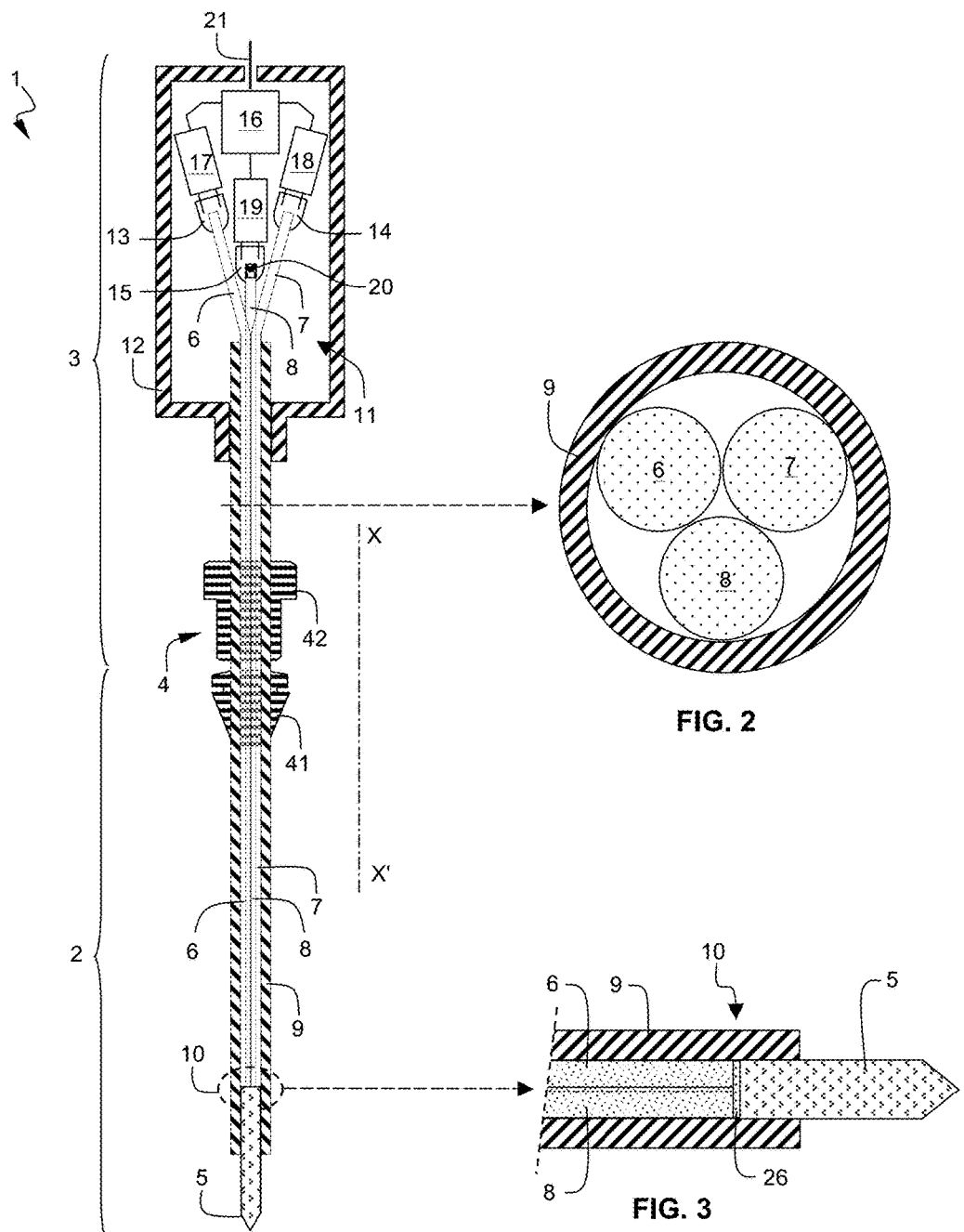

DOWNHOLE FLUID PROPERTIES ANALYSIS PROBE, TOOL AND METHOD

TECHNICAL FIELD

The invention relates to an optical analysis probe measuring downhole fluid properties based on reflectance and fluorescence. Such an optical analysis probe may be integrated in a downhole measuring tool like a production logging tool used to analyze a multiphase fluid mixture flowing from a hydrocarbon bearing zone into a hydrocarbon well. Such probes and tools operate at downhole pressure and temperature conditions.

BACKGROUND

During the production of a hydrocarbon well, it is necessary to monitor the relative volumetric flow rates of the different phases (e.g. oil, gas and water) of the multiphase fluid mixture flowing into the pipe of the well from the hydrocarbon bearing zones. Further, current hydrocarbon well often comprises vertical well section, inclined well sections and horizontal well sections. The interpretation of the flow in such complex wells is challenging because small changes in the well inclination and the flow regime influence the flow profile. Thus, an accurate monitoring requires sensors or probes capable of imaging a surface section or a volume section of the pipe and providing an estimation of the surface section or the volume section occupied by each phase.

Several sensors or probes are known in the art, for example gradiomanometer, capacitance sensors, imaging instruments comprising arrays of sensors (based on radio-frequency, X-Rays, ultrasonics, etc. . . . ), and local probes.

The document U.S. Pat. No. 6,023,340 describes single point optical probes for measuring three-phase characteristics of fluid flow in a hydrocarbon well and methods of processing signals generated by the probe. A probe having a single fiber optic is coupled to a light source and apparatus for detecting reflectance and fluorescence. Light is delivered to the tip of the probe where it either is internally reflected in the probe or exits the probe and illuminates the fluid ambient the probe tip. If the fluid at the probe tip is oil, the light exits the probe, illuminates the oil, and causes the oil to fluoresce. If the fluid is water, no fluorescence occurs. If the fluid is gas, at least some light is internally reflected in the probe. A detection system including at least one beam splitter and fluorescence and reflectance detectors is provided in conjunction with the probe. Preferably, the fluorescence detector is coupled to the fiber optic by a wavelength division multiplexer. A preferred signal processing system for detecting oil, gas, and water provides two quasi-binary indicators: gas/liquid and oil/not oil. Three of the four possible indications (gas-not oil, liquid-not oil, and liquid-oil) give results indicating whether the fluid at the probe tip is gas, water, or oil.

This optical probe comprising a single fiber results in a complex optical system that includes at least one directional coupler and a wavelength division multiplexer, or two directional couplers. As consequence, this complex optical system is difficult to integrate into a downhole measuring tool, e.g. a logging tool.

The optical analysis probe and the downhole measuring tool operate in harsh environment, namely extreme conditions including high pressure from several hundred bars up to 2000 bars, high temperature up to 200° C., presence of corrosive fluids such as sulfuric acid, presence and contamination by solid particles such as scales, asphalthenes, sand particles, as well as multiphasic flow conditions (oil, gas, water). Further, there are also the space and power constraints associated to downhole tools deployment. Furthermore, there is the high shocks environment associated to wireline or drilling or production logging operations.

SUMMARY OF THE DISCLOSURE

It is an object of the invention to propose a downhole fluid properties optical analysis probe that overcome one or more of the limitations of the existing methods and/or devices.

According to one aspect, there is provided a downhole fluid properties optical analysis probe for analyzing at least one property of a multiphase flow mixture flowing in a hydrocarbon well has an elongated cylindrical body shape and comprises:
- an optical tip at one end of the elongated cylindrical body arranged to be in contact with the multiphase flow mixture;
- an optoelectronics module at another end of the elongated cylindrical body arranged to be separated from the multiphase flow mixture and coupled to the optical tip by an optical fiber bundle; and wherein:
- the optoelectronics module comprises at least one light source arranged to emit electromagnetic radiations in a wavelength range such that reflectance occurs when gas is present at the optical tip and fluorescence occurs when oil is present at the optical tip, at least one reflectance light detector arranged to be responsive to a reflectance light and to provide a reflectance signal and at least one fluorescence light detector arranged to be responsive to a fluorescence light and to provide a fluorescence signal;
- the optical fiber bundle comprises at least one first optical fiber coupling the light source to the optical tip, at least one second optical fiber coupling the optical tip to the reflectance light detector, and at least one third optical fiber coupling the optical tip to the fluorescence light detector, the at least one first, second and third optical fibers being mounted together into a protective tube resistant to downhole conditions.

The light source may be chosen among the group comprising a laser diode, a light emitting diode, a mercury lamp, or a light bulb coupled to a filter having a wavelength ranging from 290 nm to 480 nm.

The reflectance light detector and the fluorescence light detector may be chosen among the group comprising PIN photodiodes, photoresistors, phototubes or phototransistors.

The optoelectronics module may further comprise a processing module connected to at least the reflectance light detector and the fluorescence light detector, the processing module being arranged to deliver a digital signal indicative of the oil/gas/water phases holdups and/or oil/gas bubble counts based on the reflectance signal and the fluorescence signal.

The optical tip may be a sapphire rode being needle shaped and having an external diameter ranging from around 0.3 mm to around 1 mm, the sapphire rode being partially mounted into the protective tube resistant to downhole conditions letting the distal end of the tip in contact with the multiphase flow mixture and directly contacting the at least three optical fibers at the other end.

An index gel layer may be positioned at a coupling interface between the at least three optical fibers and the other end of the optical tip.

The reflectance light detector may be associated with a low pass filter.

A low pass filter coating may be applied between an end of the third optical fiber and the fluorescence light detector.

The low pass filter coating may be a λ/4 multilayer filter.

The optoelectronics module may further comprise a third PIN photodiode that is connected to the processing module and used to estimate the leakage current of the reflectance light detector and the fluorescence light detector as a result of temperature variations.

Each of the laser diode light source, the PIN photodiode reflectance light detector and the PIN photodiode fluorescence light detector may comprise a hole machined in a front part for coupling with a corresponding optical fiber, and further comprises two terminals connected to points of connection of a printed circuit board of the optoelectronics module through a S-shaped connection wire for compensating the effect of temperature with respect to the dilatation/contraction of the connection wire and/or the printed circuit board.

At least one of the optical fibers may have at least one characteristic different from the other optical fibers, said characteristic being chosen among the group comprising diameter, structure including core, cladding, buffer and jacket, attenuation or loss in dependence of transmitted light wavelength, and material including silica, fluoride glass, phosphate glass, chalcogenide glass, plastics, doped or not.

According to a further aspect, there is provided a downhole fluid properties measuring tool comprising at least one downhole fluid properties optical analysis probe of the invention.

According to still a further aspect, there is provided a production logging tool comprising a central pressure-resistant rigid housing carrying external centralizers adapted for contact with a production pipe wall of a hydrocarbon well and at least one downhole fluid properties optical analysis probe of the invention secured on an inner face of the centralizers deploying arms such as to expose an optical tip to a multiphase fluid mixture flowing in the hydrocarbon well, an optoelectronics module of the optical analysis probe being located into said housing, a protective tube extending from the optoelectronics module to the optical tip through a pressure feedthrough into said housing.

According to still a further aspect, there is provided a downhole fluid properties optical analysis method for analyzing at least one property of a multiphase flow mixture flowing in a hydrocarbon well comprising:

illuminating the multiphase flow mixture, by means of an optical tip coupled to a light source by a first optical fiber, with electromagnetic radiations in a wavelength range such that reflectance occurs when gas is present at the optical tip and fluorescence occurs when oil is present at the optical tip;

detecting reflectance by means of a reflectance light detector coupled to the optical tip by a second optical fiber, and simultaneously detecting fluorescence by means of a fluorescence light detector coupled to the optical tip by a third optical fiber and associated with a low pass filter;

estimating oil holdup, gas holdup, and water holdup based on a comparison between said reflectance and fluorescence detection;

storing the oil/gas/water holdup estimations; and repeating the illumination step, the detection step, the estimation step and the storing step at various locations in the hydrocarbon well.

With the invention, the downhole fluid properties optical analysis probe does not comprise any directional coupler, thus achieving more accurate and stable measurements, and a more robust packaging. Further, the integration of a filter directly at the interface between the photodiode and the end of the optical fiber dedicated to fluorescence measurements enables achieving a miniature and robust packaging of the optoelectronic module. Furthermore, the integrated optoelectronic module providing direct three phase holdups and bubble counts computation enables an easy integration in an array of optical analysis probes of a production logging tool. Therefore, the downhole fluid properties optical analysis probe of the invention applies to the analysis of the optical properties of fluid flowing in hydrocarbon well. Such a probe is particularly applicable to the characterization in real time of hydrocarbon reservoir fluids (e.g. crude oil, gas, brines).

Other advantages will become apparent from the hereinafter description of the invention.

BRIEF DESCRIPTION OF THE DRAWINGS

The present invention is illustrated by way of examples and not limited to the accompanying drawings, in which like references indicate similar elements:

FIG. 1 is a partial cross-section view schematically illustrating an embodiment of a downhole fluid properties optical analysis probe;

FIG. 2 is a cross-section view perpendicularly to the longitudinal axis of the optical analysis probe of FIG. 1 in the elongated body portion of the probe;

FIG. 3 is an enlarged cross-section view along the longitudinal axis of the optical analysis probe of FIG. 1 showing the coupling interface between the optical fibers and the optical tip;

DETAILED DESCRIPTION

Figure 4:
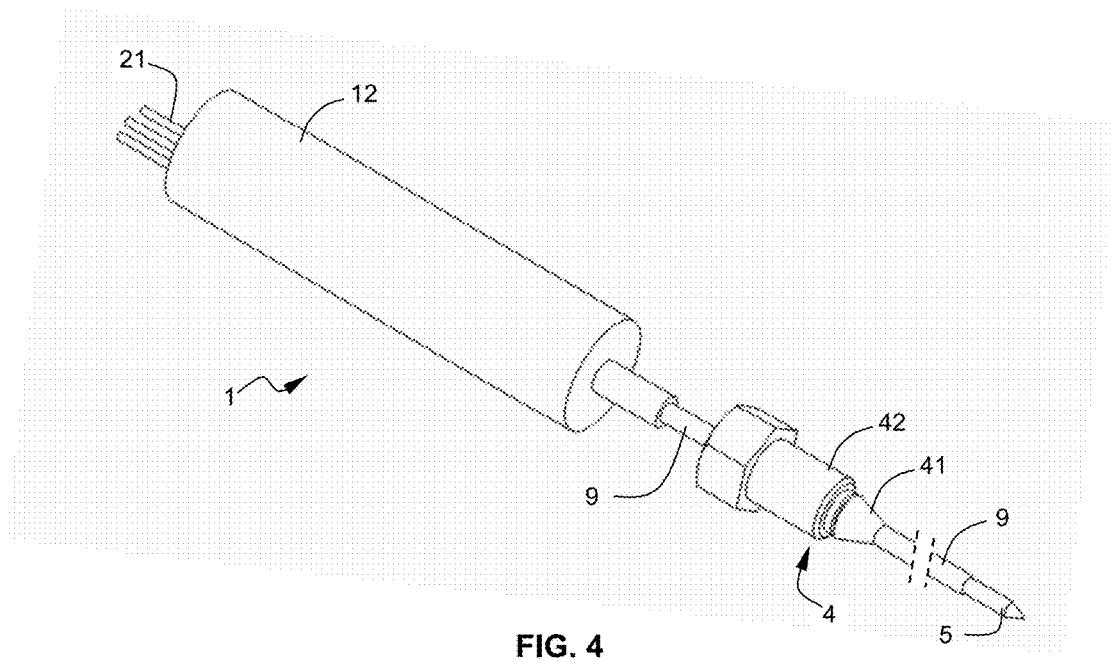
FIG. 4 is a perspective view of an assembled downhole fluid properties optical analysis probe according to the embodiment of FIG. 1.

The invention will be understood from the following description, in which reference is made to the accompanying drawings.

FIG. 1 is a partial cross-section view schematically illustrating an embodiment of a downhole fluid properties optical analysis probe 1.

The optical analysis probe 1 has the general shape of an elongated cylindrical body extending along the longitudinal axis XX'. The optical analysis probe 1 comprises a first portion 2 in contact with the well fluid to be analyzed (i.e. in contact with harsh environments), and a second portion 3 separated from the fluid to be analyzed (protected from harsh environments). A probe connector 4 separates the first portion 2 from the second portion 3.

In the first portion 2, an optical tip 5 is coupled to three optical fibers 6, 7 and 8 (e.g. silica fibers) and surrounded by a protective tube 9. FIG. 2 shows a cross-sectional area perpendicularly to the longitudinal axis XX' in the elongated body portion of the probe where the bundle of three optical fibers 6, 7 and 8 is protected by the protective tube 9.

FIG. 3 is an enlarged cross-section view along the longitudinal axis XX' showing a coupling interface 10 between the optical tip 5 and the optical fibers 6, 7 and 8. The protective tube 9 partially surrounds the optical tip 5 at the coupling interface 10, letting the distal part of the optical tip 5 in contact with the fluid to be measured.

The second portion 3 comprises an electronic board 11 and a protective housing 12. The electronic board 11 forms an optoelectronics module comprising a light source, for example an ultra-violet, violet or blue laser diode 13 (diode that emits electromagnetic radiation with a wavelength in the range 290 nm-480 nm), a first and a second photodetector, for example a first and a second PIN photodiode 14 and 15, and a processing module, for example a microcontroller 16. The violet or blue laser diode 13, the first PIN photodiode 14 and the second PIN photodiode 15 may be connected to the microcontroller 16 through corresponding amplifiers 17, 18 and 19, respectively. Each of the ultra-violet, violet or blue laser diode 13, the first PIN photodiode 14 and the second PIN photodiode 15 is connected to the optical tip 5 by a dedicated optical fiber, namely the first optical fiber 6, the second optical fiber 7 and the third optical fiber 8, respectively. A low pass filter coating 20 (for example a $\lambda/4$ multilayer filter) may be positioned between the end of the third optical fiber 8 and the second PIN photodiode 15. The low pass filter coating 20 stops the light signal in the light source emission wavelength range, but lets pass the light signal in the fluorescence wavelength range. The first optical fiber 6 is coupled to the ultra-violet, violet or blue laser diode 13. The second optical fiber 7 is coupled to the first PIN photodiode 14. The third optical fiber 8 is coupled to the second PIN photodiode 15. The microcontroller 16 is connected to cables 21 comprising a power input cable and a digital data output cable.

Though FIG. 2 shows optical fibers 6, 7 and 8 that are identical, as an alternative (not shown) the optical fibers may be of different sizes, different structures (e.g. core, cladding, buffer, jacket), different attenuations or loss in dependence of the wavelength of the particular light to be transmitted, different material (e.g. silica, fluoride glass, phosphate glass, chalcogenide glass, plastics, doped or not). In a particular configuration the optical analysis probe comprises a small diameter core fiber, for example around 50 µm, used for the transmission of the emission light from the light source and for the collection/transmission of the reflected light; and a larger diameter core fiber, for example ranging between 200 and 900 µm, used for the collection/transmission of the fluorescence light. This configuration allows a better optimization of signal to noise ratios corresponding to the differences of light power on reflectance and fluorescence collection/transmission channels.

Alternatively bundles of small size core diameter fibers where a larger number of fibers is associated to the fluorescence light collection can be used in order to achieve the same benefits.

The optical tip 5 is a sapphire rod having a needle shape. The external diameter of the sapphire rod ranges from about 0.3 mm to about 1 mm. The sapphire material has a particular robustness in corrosive environments. The needle shape has the property of fast piercing liquid interfaces and self cleaning in multiphasic conditions. At least droplets of fluids rarely stick on such a sharp tip. The angle at the end of the tip may be any angle from 30° to 90°. Alternatively, the tip may be bi-conical thus having two angles, or any other shape such as a cone with an hemispherical or rounded end. The optical tip 5 can be directly coupled to the optical fiber bundle 6, 7 and 8. As an alternative to the direct coupling between the optical fiber bundle 6, 7 and 8 and the optical tip 5, an index gel layer 26 may be positioned at the interface of these optical elements.

Figure 7A:
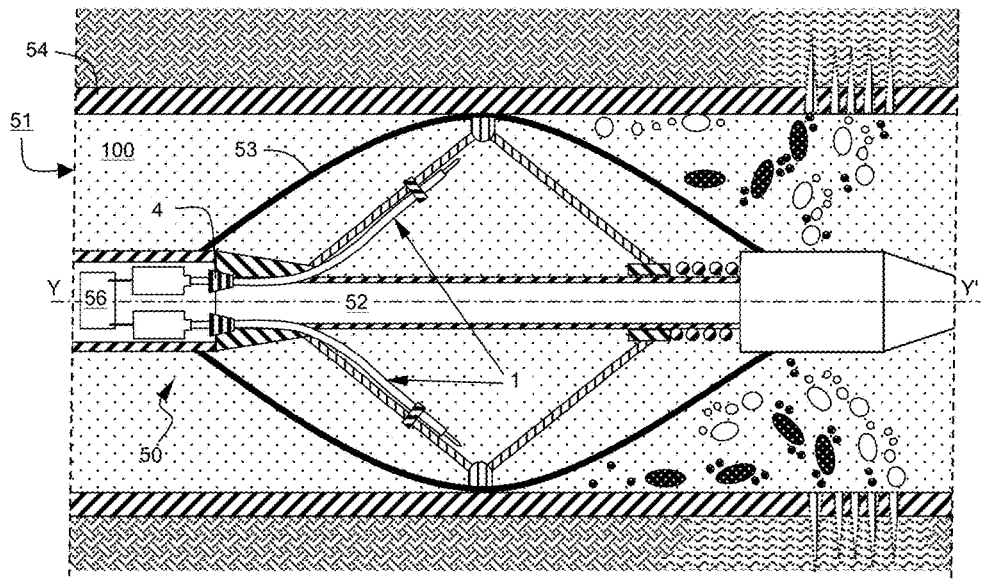
FIGS. 7a and 7b are a cross-section view and a perspective view of a downhole measuring tool like a production logging tool, respectively.
Figure 7B:
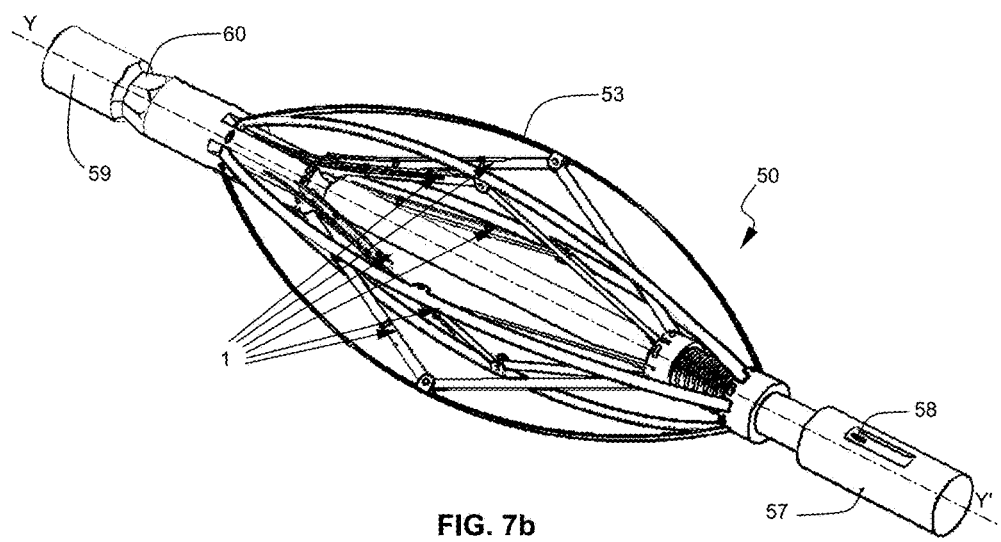

The protective tube 9 is made of metal or alloy. Metal or alloy offering high strength and high chemical resistance such as Inconel can suitably be used. The protective tube 9 is used to mechanically maintain the sapphire rod optical tip 5 ensuring a pressure tight connection to the optical fiber bundle 6, 7 and 8, to protect the optical fiber bundle 6, 7 and 8 from fluids and to hold the probe connector 4. The protective tube 9 is sealed against the optical tip 5 (for example by crimping) in order to avoid penetration of fluid towards the optical fiber bundle 6, 7 and 8 and the second portion 3. As a particular example, the protective tube 9 has an external diameter of 0.5 mm to 3 mm, and is ranging from a few centimeters to a few tens of centimeters long (e.g. 25.4 cm/10 inches). Therefore, the protective tube 9 has bending capacity that enables precisely positioning the optical tip 5 relatively to the second portion 3, in particular to position the optical tip 5 at the place where measurements are to be performed (such a capacity is illustrated in FIGS. 7a and 7b).

FIG. 4 is a perspective view of an assembled downhole fluid properties optical analysis probe 1. The probe connector 4 may slide onto the protective tube 9 and is sealed against the protective tube 9 once in place. The probe connector 4 is adapted to be connected by a screw nut type connection to a hole of a housing of a tool sub-module as depicted in FIGS. 7a and 7b. The screw nut connection may be a conical synthetic rubber/fluoropolymer elastomer ferrule 41 (metal-elastomer seal), or a conical metal ferrules 41 (metal-metal seal). For example, synthetic rubber/fluoropolymer elastomer may be Viton fluoroelastomers a registered trademark of DuPont Performance Elastomers L.L.C. A high pressure seal connection is obtained when the screw 42 associated with the conical ferule 41 both slidingly coupled to the protective tube 9 is appropriately screwed into a threaded hole. Other waterproof and high pressure connections may be appropriate, for example a screw nut connection including an O-ring. As a further alternative the connection may be a welded connection, the protective tube 9 being welded to the hole of the housing of the tool sub-module.

Figure 8A:
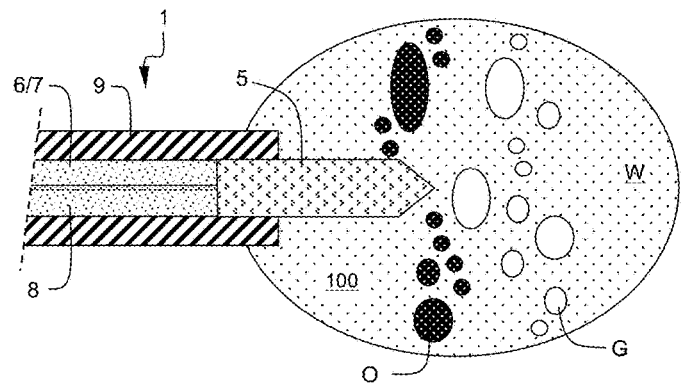
FIGS. 8a and 8b schematically illustrate the operation of the downhole fluid properties optical analysis probe.
Figure 8B:
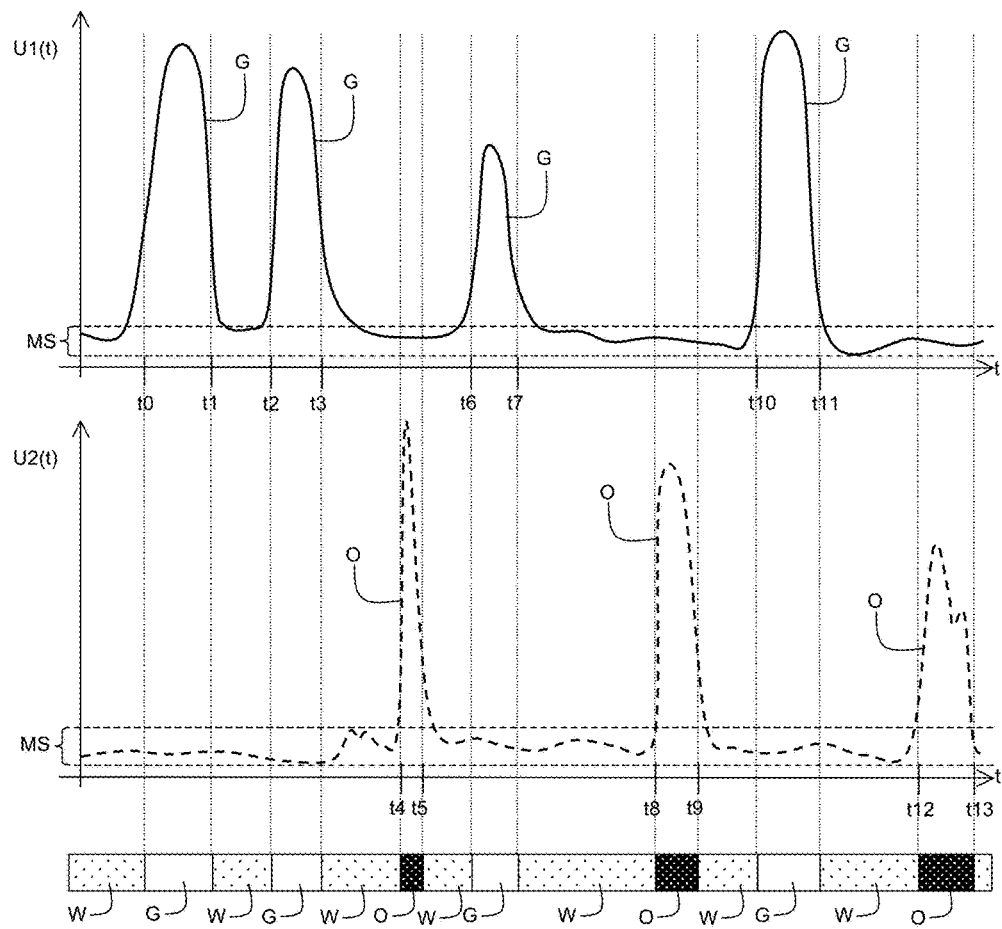

FIGS. 8a and 8b schematically illustrate the operation of the downhole fluid properties optical analysis probe. FIG. 8a shows the optical tip of the optical analysis probe 1 immerged into a multiphase fluid mixture 100. FIG. 8b illustrates the estimation of relative volumetric flow rates of different phases (e.g. oil, gas and water). The optical analysis probe 1 operates as follows. The optical analysis probe uses the fluid reflectance to derive the gas hold-up. The optical analysis probe uses the fluid fluorescence to derive the oil hold-up. In particular, the microcontroller 16 controls the emission of a violet or blue light signal by the violet or blue laser diode 13 towards the optical tip 5 through the first optical fiber 6.

When a gas bubble G is present at the tip 5, a light signal is reflected at the optical tip 5 and directed towards the reflectance light detector, e.g. the first PIN photodiode 14, through the second optical fiber 7. The first PIN photodiode 14 transforms the optical signal in an electrical signal $U1(t)$ that is amplified by the amplifier 18 and provided to the microcontroller 16. When the corresponding electrical signal at the first PIN photodiode 14 is above a mean level signal MS, a gas bubble G is detected. The microcontroller 16 further estimates the duration of the presence of the gas bubble G at the optical tip 5. In FIG. 8a—top part, gas bubbles G have been detected between the timing intervals [t0-t1], [t2-t3], [t6-t7] and [t10-t11].

When an oil bubble O is present at the tip 5, a fluorescence effect occurs and the resulting fluorescence light signal is collected at the optical tip 5 and directed towards the fluorescence light detector, e.g. the second PIN photodiode 15 and the low pass filter coating 20, through the third optical fiber 8. The second PIN photodiode 15 transforms the optical signal that has passed the low pass filter and is, thus, representative of a fluorescence effect into an electrical signal $U2(t)$. The electrical signal $U2(t)$ is amplified by the amplifier 19 and provided to the microcontroller 16. When the corresponding electrical signal at the second PIN photodiode 15 is above a mean level signal MS, an oil bubble O is detected. The microcontroller 16 further estimates the duration of the presence of the oil bubble O at the optical tip 5. In FIG. 8a—middle part, oil bubbles O have been detected between the timing intervals [t4-t5], [t8-t9] and [t12-t13].

The microcontroller 16 can then compare both signals $U1(t)$ and $U2(t)$. When not any signal above the mean level signal MS is detected by both PIN photodiodes, it means that only water W is present at the optical tip 5. Further, the microcontroller 16 can then estimate for a defined time length, the duration of gas presence versus the duration of oil presence at the optical tip 5. This is illustrated by the graphical representation in FIG. 8b—bottom part.

Figure 5:
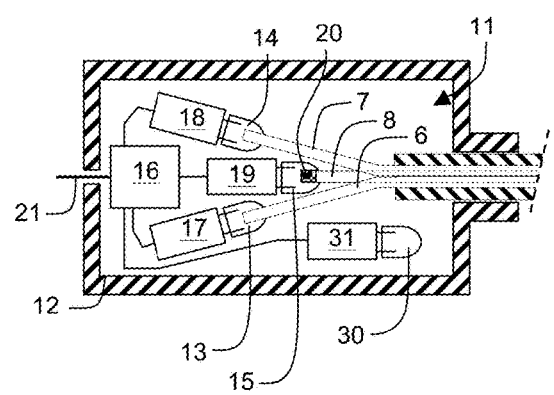
FIG. 5 schematically illustrates a second embodiment of the optoelectronics module.

FIG. 5 schematically illustrates the optoelectronics module 11 according to another embodiment. This embodiment differs from the one of FIG. 1 in that the optoelectronics module further comprises a third photodetector 30, for example a PIN photodiode that is connected to the microcontroller 16 via a fourth amplifier 31. The third photodetector 30 is not coupled to any optical fiber and is used to estimate the leakage current of the PIN photodiode as a result of the variation of temperature within de protective housing 12. Leakage current effect and its variation with temperature can be directly eliminated, or greatly reduced, by adding this additional photodetector on the amplifier circuit. Based on this estimation, the microcontroller 16 determines the slow fluctuation of the mean level signal (MS visible in FIG. 8b) measured by the first and second PIN photodiodes 14 and 15.

Figure 6:
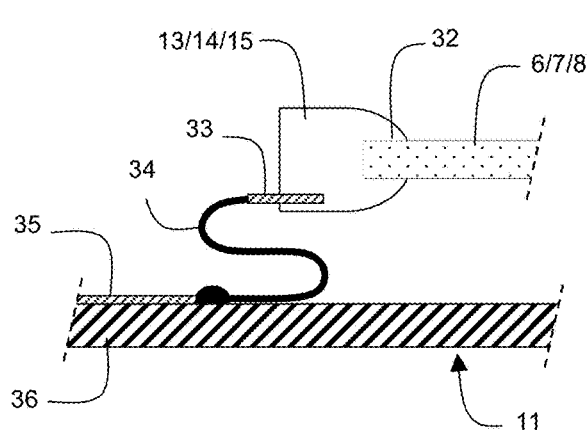
FIG. 6 schematically illustrates temperature induced stress compensated connection of the diode to the printed circuit board of the optoelectronics module.

FIG. 6 schematically illustrates a temperature induced stress compensated connection of the diodes 13, 14 and 15 to the printed circuit board 36 of the optoelectronics module 11. Each diode (ultra-violet, violet or blue laser diode 13 and PIN photodiodes 14 and 15) comprises a hole 32 machined in the front part for coupling with the corresponding optical fiber (first optical fiber 6, and second and third optical fiber 7 and 8, respectively). Each of the two terminals of each diode (only one terminal 33 is visible in FIG. 6) is connected to a point of connection (only one point of connection 35 is visible in FIG. 6) of the Printed Circuit Board (PCB) 36 of the optoelectronics module 11 through a S-shaped connection wire 34. The S-shaped connection wire 34 enables compensating the effect of temperature with respect to the dilatation/contraction of the whole assembly, in particular leading to displacement of the fiber end position with respect to the PCB. Therefore, each diode follows the same displacement as the corresponding optical fiber and a stable light transmission between the diode and the corresponding optical fiber or vice-versa is achieved.

FIGS. 7a and 7b are a cross-section view and a perspective view of a downhole measuring tool like a production logging tool unit 50 adapted for operation in a hydrocarbon producing well 51, respectively.

Multiple optical probes 1 are mounted in the production logging tool unit 50 used for production evaluation of hydrocarbon wells. Generally, the production logging tool unit 50 also comprises other kinds of sensor/probe like pressure, temperature and flow sensors. The production logging tool unit 50 has a central pressure-resistant rigid housing 52 that carries external centralizers 53 adapted for contact with the production pipe walls 54 of the well 51. Multiple optical probes 1 (first portion 2) as described above are secured on the inner face of the centralizers 53 deploying arms, for example by attaching the protective tube 9 such as to expose the optical tip 5 to the multiphase fluid mixture 100. The optical probes 1 may be located at angularly distributed locations with respect to the central axis YY' of the production logging tool unit 50. Such a distributed probes arrangement solves the issue of measurement representativeness in inhomogeneous fluid flow as multiple measurements by multiple local probes become representative of the overall fluid flowing into the conduit of the well 51. Each optical probe 1 (second portion 3) are connected through a pressure feedthrough, for example the probe connector 4 into the housing 52 such that the electronic board 11 and the protective housing 12 are located inside the housing 52 of the production logging tool 50. The electronic board 11 is connected to a power and processing circuit 56 that delivers power to the optical probe 1 and receives local downhole fluid properties measured by each optical probe 1. The production logging tool unit depicted in FIG. 9b may be connected endwise to various sections carrying other types of fluid sensors such as pressure sensors 57, temperature sensors 58, flowrate sensors 59 and imager 60.

Multiple production logging tool units may assembled together in a string (not shown). Using at least two production logging tool units allows cross correlation measurement on fluid holdups. Hydrocarbon wells production fluctuates with time, generating slugs and/or clouds of droplets or bubbles which propagate along the well. Measuring those corresponding variations using the optical probes of the invention installed in at least two units allows deducing dispersed phase velocity and interpreting critical production parameter such as water, oil, gas entries in specific well sections.

The drawings and their description hereinbefore illustrate rather than limit the invention.

It should be appreciated that embodiments of the optical analysis probe of the invention is not limited to light source being a laser diode and light detector being a PIN photodiode. Other kinds of light source are applicable, namely light emitting diodes, mercury lamps, or light bulbs coupled to filters so as to emit a light in a wavelength ranging from 290 nm to 480 nm. Other kinds of light detector are applicable, namely PIN photodiodes, photoresistors, phototubes or phototransistors that are responsive to the specific reflectance light or fluorescence light. Further, the use of a low pass filter is only related to a specific embodiment comprising a standard PIN photodiode because when the corresponding fluorescence light detector is only responsive to a fluorescence light, the low pass filter is not anymore necessary.

It should be appreciated that embodiments of the production logging tool according to the present invention are not limited to the embodiment showing horizontal hydrocarbon well bore, the invention being also applicable whatever the configuration of the well bore, namely vertical, inclined or a combination of vertical, inclined and/or horizontal portions, cased or uncased. Also, the optical analysis probe of the invention is not limited to an application into a production logging tool, but can be easily adapted to various applications into analysis tools operating at downhole pressure and temperature conditions, e.g. a downhole fluid analysis tool, a wireline tool, a logging while drilling tool, a formation tester.

The invention claimed is:

1. A downhole fluid properties optical analysis probe for analyzing at least one property of a multiphase flow mixture flowing in a hydrocarbon well having an elongated cylindrical body shape and comprising:
an optical tip at one end of the elongated cylindrical body arranged to be in contact with the multiphase flow mixture; and
an optoelectronics module at another end of the elongated cylindrical body arranged to be separated from the multiphase flow mixture and coupled to the optical tip by an optical fiber bundle;
and wherein:
the optoelectronics module comprises at least one light source arranged to emit electromagnetic radiations in a wavelength range such that reflectance occurs when gas is present at the optical tip and fluorescence occurs when oil is present at the optical tip, at least one reflectance light detector arranged to be responsive to a reflectance light and to provide a reflectance signal and at least one fluorescence light detector arranged to be responsive to a fluorescence light and to provide a fluorescence signal;
the optical fiber bundle comprises at least one first optical fiber coupling the light source to the optical tip, at least one second optical fiber coupling the optical tip to the reflectance light detector, and at least one third optical fiber coupling the optical tip to the fluorescence light detector, the at least one first, second and third optical fibers being mounted together into a protective tube resistant to downhole conditions.

2. The optical analysis probe of claim 1, wherein:
the light source is chosen among the group comprising a laser diode, a light emitting diode, a mercury lamp, or a light bulb coupled to a filter having a wavelength ranging from 290 nm to 480 nm;
the reflectance light detector and the fluorescence light detector are chosen among the group comprising PIN photodiodes, photoresistors, phototubes or phototransistors.

3. The optical analysis probe of claim 2, wherein the optoelectronics module further comprises a processing module connected to at least the reflectance light detector and the fluorescence light detector, the processing module being arranged to deliver a digital signal indicative of the oil/gas/water phases holdups and/or oil/gas bubble counts based on the reflectance signal and the fluorescence signal.

4. The optical analysis probe of claim 3, wherein an index gel layer is positioned at a coupling interface between the at least three optical fibers and the other end of the optical tip.

5. The optical analysis probe of claim 2, wherein each of the laser diode light source, the PIN photodiode reflectance light detector and the PIN photodiode fluorescence light detector comprises a hole for coupling with a corresponding optical fiber, and further comprises two terminals connected to points of connection of a printed circuit board of the optoelectronics module through a S-shaped connection wire for compensating the effect of temperature with respect to the dilatation/contraction of the connection wire and/or the printed circuit board.

6. The optical analysis probe of claim 1, wherein the optoelectronics module further comprises a processing module connected to at least the reflectance light detector and the fluorescence light detector, the processing module being arranged to deliver a digital signal indicative of the oil/gas/water phases holdups and/or oil/gas bubble counts based on the reflectance signal and the fluorescence signal.

7. The optical analysis probe of claim 1, wherein the optical tip is a sapphire rod being needle shaped and having an external diameter ranging from around 0.3 mm to around 1 mm, the sapphire rod being partially mounted into the protective tube resistant to downhole conditions letting the distal end of the tip in contact with the multiphase flow mixture and directly contacting the at least three optical fibers at the other end.

8. The optical analysis probe of claim 1, wherein the reflectance light detector is associated with a low pass filter.

9. The optical analysis probe of claim 1, wherein a low pass filter coating is applied between an end of the third optical fiber and the fluorescence light detector.

10. The optical analysis probe of claim 9, wherein the low pass filter coating is a $\lambda/4$ multilayer filter.

11. The optical analysis probe of claim 1, wherein the optoelectronics module further comprises a third PIN photodiode connected to the processing module and used to estimate the leakage current of the reflectance light detector and the fluorescence light detector as a result of temperature variations.

12. The optical analysis probe of claim 1, wherein at least one of the optical fibers has at least one characteristic different from the other optical fibers, said characteristic being chosen among the group comprising diameter, structure including core, cladding, buffer and jacket, attenuation or loss in dependence of transmitted light wavelength, and material including silica, fluoride glass, phosphate glass, chalcogenide glass, plastics, doped or not.

13. A downhole fluid properties measuring tool comprising at least one downhole fluid properties optical analysis probe for analyzing at least one property of a multiphase flow mixture flowing in a hydrocarbon well,
wherein said, at least one optical analysis probe has an elongated cylindrical body shape and comprises:
an optical tip at one end of the elongated cylindrical body arranged to be in contact with the multiphase flow mixture; and
an optoelectronics module at another end of the elongated cylindrical body arranged to be separated from the multiphase flow mixture and coupled to the optical tip by an optical fiber bundle;
the optoelectronics module comprising at least one light source arranged to emit electromagnetic radiations in a wavelength range such that reflectance occurs when gas is present at the optical tip and fluorescence occurs when oil is present at the optical tip, at least one reflectance light detector arranged to be responsive to a reflectance light and to provide a reflectance signal and at least one fluorescence light detector arranged to be responsive to a fluorescence light and to provide a fluorescence signal;
the optical fiber bundle comprising at least one first optical fiber coupling the light source to the optical tip, at least one second optical fiber coupling the optical tip to the reflectance light detector, and at least one third optical fiber coupling the optical tip to the fluorescence light detector, the at least one first, second and third optical fibers being mounted together into a protective tube resistant to downhole conditions.

14. A production logging tool comprises a central pressure-resistant rigid housing carrying external centralizers adapted for contact with a production pipe wall of a hydrocarbon well and at least one downhole fluid properties optical analysis probe for analyzing at least one property of a multiphase flow mixture flowing in a hydrocarbon well, wherein said, at least one optical analysis probe has an elongated cylindrical body shape and comprises:

an optical tip at one end of the elongated cylindrical body arranged to be in contact with the multiphase flow mixture;

an optoelectronics module at another end of the elongated cylindrical body arranged to be separated from the multiphase flow mixture and coupled to the optical tip by an optical fiber bundle;

the optoelectronics module comprising at least one light source arranged to emit electromagnetic radiations in a wavelength range such that reflectance occurs when gas is present at the optical tip and fluorescence occurs when oil is present at the optical tip, at least one reflectance light detector arranged to be responsive to a reflectance light and to provide a reflectance signal and at least one fluorescence light detector arranged to be responsive to a fluorescence light and to provide a fluorescence signal;

the optical fiber bundle comprising at least one first optical fiber coupling the light source to the optical tip, at least one second optical fiber coupling the optical tip to the reflectance light detector, and at least one third optical fiber coupling the optical tip to the fluorescence light detector, the at least one first, second and third optical fibers being mounted together into a protective tube resistant to downhole conditions;

and wherein said, at least one optical analysis probe is secured on an inner face of the centralizers deploying arms such as to expose the optical tip to the multiphase fluid mixture flowing in the hydrocarbon well, the optoelectronics module of the downhole fluid properties optical analysis probe being located into said housing, the protective tube extending from the optoelectronics module to the optical tip through a pressure feedthrough into said housing.

15. A method for analyzing at least one property of a multiphase flow mixture flowing in a hydrocarbon well comprising:

illuminating the multiphase flow mixture, by means of an optical tip coupled to a light source by a first optical fiber, with electromagnetic radiations in a wavelength range such that reflectance occurs when gas is present at the optical tip and fluorescence occurs when oil is present at the optical tip;

detecting reflectance by means of a reflectance light detector coupled to the optical tip by a second optical fiber, and simultaneously detecting fluorescence by means of a fluorescence light detector coupled to the optical tip by a third optical fiber and associated with a low pass filter;

estimating oil holdup, gas holdup, and water holdup based on a comparison between said reflectance and fluorescence detection;

storing the oil/gas/water holdup estimations; and repeating the illumination step, the detection step, the estimation step and the storing step at various locations in the hydrocarbon well.

* * * * *